United States Patent [19]

Zajic et al.

[11] 3,997,398
[45] Dec. 14, 1976

[54] EMULSIFYING AGENTS OF MICROBIOLOGICAL ORIGIN

[75] Inventors: James E. Zajic, London; Eva Knettig, Sarnia, both of Canada

[73] Assignee: Canadian Patents and Development Limited, Ottawa, Canada

[22] Filed: June 27, 1974

[21] Appl. No.: 483,590

Related U.S. Application Data

[63] Continuation-in-part of Ser. No. 285,159, Aug. 31, 1972, abandoned.

[52] U.S. Cl. .......................... 195/28 R; 195/31 P
[51] Int. Cl.² ..................................... C12B 1/00
[58] Field of Search ............... 195/3 H, 28 R, 100, 195/29, 31 P; 252/351, 352, 8.55 C, 356, 357; 260/209.6, 210

[56] References Cited

UNITED STATES PATENTS

| 3,096,293 | 7/1963 | Jeanes et al. | 252/8.5 C |
| 3,406,114 | 10/1968 | Goren | 195/31 P |
| 3,655,512 | 4/1972 | Tanaka et al. | 195/28 R |

*Primary Examiner*—R. B. Penland
*Attorney, Agent, or Firm*—Hirons & Rogers

[57] ABSTRACT

An emulsifying agent of microbiological origin is produced by an aerobic aqueous fermentation process employing Corynebacterium hydrocarboclastus UWO 409 as the fermentation agent and paraffinic hydrocarbon substrate. An emulsifying agent product consists essentially of an extracellular polymer product of a fermentation process, the polymer comprising a polysaccharide component including galactose, glucose and mannose in ratio about 1:2.65:1.96 and a bound protein component.

15 Claims, No Drawings

EMULSIFYING AGENTS OF MICROBIOLOGICAL ORIGIN

CROSS REFERENCE TO RELATED APPLICATIONS

This application is a continuation in part of our application SER. No. 285,159, filed Aug. 31st, 1972, now abandoned.

FIELD OF THE INVENTION

The present invention is concerned with improvements in or relating to emulsifying agents produced by microbiological processes.

REVIEW OF THE PRIOR ART

There has been a constant search for new emulsifying agents in view of the many valuable ways in which they can be used. One example of such a use is in the dispersal of oil spills on sea and land, the emulsifying action of the agent considerably enlarging the surface area of the spilled material to corespondingly increase the natural rate of oxidation and biodegradation. Such use of an emulsifying dispersant on a large spill is extremely expensive and many of the most readily available materials have unknown or even toxic effects upon the local flora and fauna.

DEFINITION OF THE INVENTION

It is the principal object of the present invention to provide new emulsifying agents which are of microbiological origin.

It is a more specific object to provide such new agents which are particularly suitable for the emulsification of high carbon fuels such as kerosene and Bunker C oil.

In accordance with the present invention there is provided a process for the production of an emulsifying agent of microbiological origin comprising the step of cultivating by an aerobic fermentation in aqueous solution and with paraffinic hydrocarbon substrate as principal source of assimilable carbon a microorganism of species Corynebacterium hydrocarboclastus of the type UWO 419 or NRRL-B-5631 until the fermentation medium contains at least 0.1% by weight of an active emulsification agent consisting of an extra-cellular polymer formed as a result of the fermentation.

Also in accordance with the invention there is provided an emulsifying agent of microbiological origin consisting essentially of the extra-cellular polymer product of an aqueous aerobic fermentation employing a microorganism of species Corynebacterium hydrocarboclastus with paraffinic hydrocarbon substrate, the said polymer comprising a polysaccharide component including primarily galactose, glucose and mannose in the ratio about 1:2.65:1.96 and a bound protein component, the polymer containing about 1 to 4% by weight organic nitrogen and about 30 to 35% by weight carbohydrate.

Preferably the said extra-cellular polymer comprises a polysaccharide component including galactose, glucose and mannose.

Preferably the molecular weight of the product is greater than 20,000.

DESCRIPTION OF THE PREFERRED EMBODIMENT

In a process for producing an emulsifying agent in accordance with the invention the culture Corynebacterium hydrocarboclastus, the taxonomic description of which is given below, is cultivated with a long chain paraffinic hydrocarbon substrate in a suitable aqueous nutrient medium.

The nutrient medium consisted of a solution in tap water of the following by weight:

| | |
|---|---|
| NaNO$_3$ | 0.5% |
| K$_2$HPO$_4$ | 0.5% |
| Yeast extract | 0.3% |
| KH$_2$PO$_4$ | 0.2% |
| MgSO$_4$ | 0.2% |
| NaCl | 0.1% |

Under laboratory conditions about 15 litres of this solution were added to a 24 liter fermentation vessel, together with about 5% by volume of culture inoculum and about 1.5% by weight of kerosene. The pH of the contents was adjusted to 6.5 – 6.8. The temperature was controlled at 28°±0.5° C, aeration was supplied by bubbling air therethrough at 5 litre/min., while the contents were agitated vigorously by an impeller operating at 500 r.p.m. A standard plot of cell growth against time gives a sigmoid curve with the exponential phase completed in 60 hours.

The fermentation broth itself may be used as an emulsifying agent in accordance with the invention, and may be freeze dried directly for storage purposes, or the active principle comprising an extracellular polymer that accompanies the cell formation may be separated from the broth. In a typical separation any unused kerosene is removed from the broth by extraction with ether or chloroform, and thereafter the cellular component is removed by centrifuging (e.g. at 10 – 12,000 r.p.m. in a Sorvall centrifuge for 30 – 60 mins.) The cellular mass is dried overnight and weighed to determine yield.

The impure polymer also is effective as an emulsification agent and may be recovered from the supernatent liquid of the centrifugate by precipitation at pH 3.0 – 6.5 with two or more volumes of alcohol, acetone or similar solvents. The polymer is soluble in water and weak or strong acids or bases. The precipitation starts at pH 5.0 and no precipitation occurs at pH 7.0.

If desired the polymer can be purified by redissolving in water, if necessary, dialysation with water and subsequent removal of low molecular weight contaminants, particularly those with molecular weight less than 20,000 by first filtration through a Millipore filter of 1.2 $\mu$ and 0.45 $\mu$ pore size and then by use of an ultra filter with Diaflo membrane PM-30 or XM-50. The purified agent is reprecipitated and the solvent removed under vacuum at slightly elevated temperature, or by use of dry heat at temperatures less than 130° C.

The synthesis of the extracellular polymer appears to be associated quantitatively directly with that of the cellular material, so that cell growth must be increased to obtain higher polymer production.

The production of cellular material obtained was 10 – 13 grams/litre, which corresponds to a yield of 67 – 87% by weight of hydrocarbon supplied, while the polymer was produced at 5.0 – 6.0 grams/litre, which corresponds to 37 – 40% by weight of the hydrocarbon. The rate of cell production in an exponential phase was 0.27 g/litre hr., while the corresponding rate of polymer formation was 0.25 g/litre hr.

The polymer emulsifying agent component possesses many characteristics of a polysaccharide but it also contains a bound protein component. The polymer contains 1 – 3% organic nitrogen as determined by Kjeldahl by the method described by Welcher (1962). The carbohydrate content is 30 – 35% as determined colorimetrically using anthrone reagent and expressed as glucose equivalent (Morris, 1948). Hydrolysis of the polymer yields 0.015% phosphorus as determined colorimetrically using stannous chloride reagent. The polysaccharide component consisted of galactose, glucose and mannose in the ratio 1:2.65:1.96, traces of arabinose and xylose and a hexuronic acid expressed as glucuronic acid equivalent. All have been identified by paper chromatographic techniques and gel filtration. Monomers were identified by spraying with p-anisidine hydrochloride (Hough et al, 1950), 1.0% potassium permanganate in 2.0% sodium carbonate (Pascu et al, 1949), benzidine (Horrocks, 1949) and glucuronic acid using naphtharescorcinol reagent (Hawk et al, 1951).

The amino acid content of the protein part of the polymer was determined from acid hydrolysate (100° C, 24 hr. in 5.7 N HCl, sample hydrolyzed in 60%) by use of an automatic amino acid analyzer. In addition, many were identified by paper chromatography. These are summarized in Table 1 below.

TABLE 1

| AMINO ACID | % IN HYDROLYZED PROTEIN | |
|---|---|---|
| | SAMPLE 1 | SAMPLE 2 |
| aspartic acid | 12.20 | 11.44 |
| threonine | 7.91 | 7.61 |
| serine | 8.36 | 8.74 |
| glutamic acid | 10.34 | 9.68 |
| glutamine | 1.91 | 2.60 |
| proline | 2.39 | 2.50 |
| glycine | 14.19 | 13.28 |
| alanine | 13.16 | 12.56 |
| cystine | trace | trace |
| valine | 1.81 | 1.98 |
| methionine | 4.68 | 5.33 |
| isoleucine | 2.89 | 2.95 |
| leucine | 7.63 | 7.65 |
| tyrosine | 2.56 | 2.83 |
| phenylalanine | 3.15 | 3.51 |
| histidine | 3.10 | 3.76 |
| ornithine | 0.70 | 0.55 |
| lysine | 3.02 | 3.03 |
| arginine | trace | trace |

INFRA-RED ANALYSIS

Highly purified polymer was subject to infra-red analysis. The polymer was purified by continued dialysis through a Diaflo membrane XM50 ultrafilter, the remaining emulsifying agent having a mol. wt of approximately 50,000 was freeze dried and analyzed by IR using the KBr pellet method. The spectrum is shown in Table 2 along with a tabular interpretation.

The spectra indicates the emulsifier is a complex material of a high molecular weight containing phosphate, amino nitrogen, carboxyl and hydroxyl groups.

TABLE 2

| Approximate Position of Bands Maximum; Wavelength, $\mu$ | Vibrating Groups Most Probably Giving Rise to Observed Absorption Band |
|---|---|
| 2.95 | free OH or bounded OH stretching of polymers, (free) NH stretching |
| 3.4 and 3.5 | C—H stretching ($CH_3$ or $CH_2$) |
| 4.3 | P—H stretching ? |
| 5.3 | ? |
| 6.0 | absorbed water and C = 0 stretching |
| 6.05 and 6.45 | amide bands (NH) |
| 6.2 | $COO^-$-carboxylate ions stretching |
| 7.15 and 8.1 | acetyl group |
| 8.7 | CHOH stretching |
| 9.3 | OH bending |
| 9.5 | C—OH stretching |
| 10.9 and 11.3 | C—H stretching |

Many different preparations of emulsifying agents were prepared for making comparisons in their elemental analysis. Crude polymer is that precipitated directly from broth with either alcohol or acetone. After precipitation the polymer was chloroform extracted, chloroform-methanol extracted, dialyzed using distilled water and an XM100 membrane (mol wt<100,000). For each preparation the percentage nitrogen, corresponding percentage protein and percentage sugar was determined. The resulting data are summarized in Table 3.

TABLE 3

| Preparation | %N* | N expressed as % protein | % Sugar** |
|---|---|---|---|
| Crude Polymer | 4.2 | 26 | 34 |
| Chloroform extract | 3.5 | 22 | 36 |
| Chloroform-methanol (2:1) extract | 1.5 | 9.5 | 43 |
| Diethyl ether extract | 2.4 | 15.5 | 38 |
| Dialyzed-XM100 (>100,000 mol wt) | 1.3 | 9.0 | 50 |

*Elemental N determined by automatic analyzer
**Sugar determined by colorimetric reaction with antrone reagent and expressed as glucose equivalent An automatic carbon-hydrogen analyzer was used to analyze the most purified fraction (dialyzed-XM100), i.e. greater than 100,000 mol. wt. The carbon content was calculated to be 43.5% and the hydrogen 10.5%. Typical hexose carbohydrates contain ~ 40% C; ~ 6.6% H and typical proteins contain ~ 50% C; ~ 7% H. The highly purified polymer contained 0.015% phosphorus by the colorimetric method of Ernster. To show the presence of phosphorus the emulsifying agent had to be hydrolyzed since non-hydrolyzed material gave no reaction. Upon ashing the purified emulsifier, approximately 10% ash was obtained for dialyzed samples and approximately 1% ash for samples precipitated by alcohol.

The following tables illustrate typical optimum conditions for maximizing the production of the polymer material accompanied by corresponding cellular production.

Table 4 shows the yields obtained in shake flasks with longchain paraffinic hydrocarbons of 11 – 20 carbon atoms.

TABLE 4

| Paraffinic hydrocarbon | Cellular Yield g/100 ml dry wt | Polymer yield g/100 ml dry wt | pH |
|---|---|---|---|
| $C_{11}$ | 0.038 | 0.028 | 5.3 |

TABLE 4-continued

| Paraffinic hydrocarbon | Cellular Yield g/100 ml dry wt | Polymer yield g/100 ml dry wt | pH |
|---|---|---|---|
| $C_{12}$ | 0.054 | 0.054 | 5.0 |
| $C_{13}$ | 0.054 | 0.053 | 4.7 |
| $C_{14}$ | 0.027 | 0.035 | 4.6 |
| $C_{15}$ | 0.030 | 0.093 | 4.7 |
| $C_{16}$ | 0.022 | 0.048 | 5.0 |
| $C_{17}$ | 0.005 | 0.026 | 4.6 |
| $C_{18}$ | 0.022 | 0.044 | 4.5 |
| $C_{19}$ | 0.059 | 0.039 | 5.7 |
| $C_{20}$ | 0.064 | 0.023 | 4.7 |

These figures were obtained using a nutrient medium in which ammonium sulphate was used as a source of nitrogen and not sodium nitrate. As the ammonium is utilized the pH of the system decreases and inhibits growth. The production of polymer with ammonium sulphate is poor and sodium nitrate is preferred.

Table 5 below shows the effect of varying amounts of kerosene present in the culture medium, as a typical mixture of long chain paraffinic hydrocarbons.

TABLE 5

| % kerosene vol/vol | % kerosene wt/wt | cellular dry wt gm/liter | polymer dry wt gm/liter |
|---|---|---|---|
| 0.5 | 0.375 | 3.0 | 2.0 |
| 1.0 | 0.75 | 6.0 | 3.5 |
| 1.5 | 1.125 | 9.0 | 4.2 |
| 2.0 | 1.5 | 12.0 | 4.5 |
| 3.0 | 2.25 | 14.0 | 6.5 |
| 4.0 | 3.0 | 16.0 | 7.0 |
| 5.0 | 3.75 | 15.0 | 4.8 |

It will be seen that a maximum was obtained at 4.0% kerosene. However in a batch fermentation an economical operating range for optimum yields is found to be between 1 and 2% by volume. Considerably more than 5% may be employed and up to 10% of paraffinic hydrocarbon, either by volume or by weight, may be added.

Table 6 below shows the effect of the addition of yeast extract to the nutrient medium. The experiments were conducted with shake flasks and an incubation period of 10 days.

TABLE 6

| % yeast extract wt/wt | cellular dry wt gm/liter | polymer dry wt gm/liter |
|---|---|---|
| 0 | 4.0 | 3.0 |
| 0.1 | 9.0 | 5.3 |
| 0.2 | 10.0 | 5.6 |
| 0.3 | 11.0 | 6.0 |
| 0.4 | 9.7 | 5.7 |
| 0.5 | 9.0 | 5.0 |

It will be seen that growth and polymer production increase enormously with the addition of yeast extract, but a peak is reached at about 3% by weight, and thereafter a decrease from the maximum is obtained.

Table 7 below shows the effect of varying the percentage of inoculum added, the inoculum used being 7 days old. A separate series of experiments showed that the inoculum should be at least 5 days old. There is a steady increase of yield with increase of inoculum.

TABLE 7

| % inoculum by vol. | cellular dry wt gm/liter |
|---|---|
| 1 | 7.5 |
| 3 | 8.6 |
| 5 | 9.5 |
| 7 | 10.0 |
| 10 | 10.8 |

As indicated above, the fermentation broth, the precipitated polymer and the isolated polymer are all usable and highly effective as emulsifying agents for long chain paraffinic hydrocarbons (e.g. of carbon content greater than 10), particularly fuels such as kerosene and Bunker C fuel oil.

The experiments for determining emulsification characteristics were carried out in two stages: (1) emsulsification of kerosene and Bunker C oil in distilled water, (2) emulsification of Bunker C oil in artificial sea water at different temperatures. Each of the emulsifying products was dissolved and/or suspended, as the case may be, in distilled in water were placed in 500 ml Erlenmeyer flasks and specified dosages of either kerosene or Bunker C oil added. Agitation was supplied by placing mixtures on a New Brunswick rotary shaker at 200 ppm (~25° C). The oil droplets from the emulsion were measured under a microscope after 24 hours. For this purpose the emulsion was stabilized in gelatin using the technique described by Katinger et al., 1970. One hundred droplets of oil from the sample were informatively measured and the droplet size distribution was statistically evaluated by using a computer program. The kerosene used in the experiment contained primarily dodecane, tridecane, tetradecane and pentadecane. The Bunker C fuel oil contained 34.2% of saturates, 38% aromatics, 18.8% polar compounds, 9% asphaltenes and 1.66% sulphur on a weight basis. Its viscosity at 15° C was 460 poises. Artificial sea water medium (McLachlan, 1959) was used.

Table 8 below shows the results of using the purified polymer as an emulsifying agent. The purified polymer in concentrations of 0.001, 0.01, 0.02 and 0.05% by weight were added to water (w/w) and used to emulsify kerosene. The kerosene levels tested were 5, 10 and 30% (v/v). Droplet size depended on whether the sample was removed from the top or bottom of the test vessel. It also was dependent upon the concentration of polymer added and the dosage of kerosene. At .001% concentration polymer droplet formation is restricted to the top area, whereas at 0.01% large droplets of 1–4 mm are found in the top area and small droplets of 4.17–5.3 $\mu$ are found in the bottom layer. At .05% polymer upper and bottom zones are lost and an homogenous emulsion is observed (3.9–5.66 $\mu$).

TABLE 8

| Emulsifier in Water % (w/w) | Kerosene % (v/v) | Type of Emulsion | Droplet size (diameter) | |
|---|---|---|---|---|
| | | | Top * | Bottom ** |
| 0.001 polymer | 5, 10 and 30 | A signification for emulsification in top oil layer | — | — |

TABLE 8-continued

| Emulsifier in Water % (w/w) | Kerosene % (v/v) | Type of Emulsion | Droplet size (diameter) | |
|---|---|---|---|---|
| | | | Top * | Bottom ** |
| 0.01 polymer | 5 10 30 | Two emulsions were formed: top emulsion rich on oil phase with big droplets and bottom emulsion with fine droplets of oil dispersed in water phase | 1-4 mm | 4.17 μ 4.25 μ 5.30 μ |
| 0.02 polymer | 5, 10 and 30 | The same as with 0.01% polymer in water | + | + |
| 0.05 polymer | 5 10 30 | A homogenous emulsion | | 3.91 μ 3.99 μ 5.66 μ |

\* by visual observation
\*\* arithmetic mean diameter from statistical evaluation of 100 droplets measured under microscope
− no emulsification observed
+ droplets not measured These same indicia are used also in Tables 9 to 11.

Tables 9 and 10 below show the emulsification of Bunker C fuel oil respectively with purified polymer and fermentation broth. The concentrations of fermentation broth tested were 0.05, 0.1, 0.5, 1.0, 2.0 and 3.0% (w/w) The levels of Bunker C oil used were 5 and 10% (v/v). At .01% purified polymer, the emulsification starts but oil and water separate upon standing. There is a considerable amount of Bunker C adhering to the glass surface in all test samples except at .05% polymer where the oil is almost completely emulsified.

At .05% purified polymer and at either 5 or 10% Bunker C oil the droplet size at the top of the vessel was 2.5 mm whereas sample from the bottom shows an average droplet size of 1.7μ. The fermentation broth containing polymer and cells of c. hydrocarboclastus also gives good emulsification. Addition of 1.0 and 2.0% fermentation broth to water (w/w) was equivalent in emulsification capability to .05% polymer. Under these conditions, the droplets of Bunker C oil were smaller than those observed with kerosene.

TABLE 9

| Emulsifier in Water % (w/w) | "Bunker C" oil % (v/v) | Type of Emulsion | Droplet size (diameter) | |
|---|---|---|---|---|
| | | | top * | bottom ** |
| 0.001 polymer | 5 and 10 | No emulsification, heavy deposit of oil on walls | − | − |
| 0.001 polymer | 5 and 10 | A signification for emulsification in bottom water layer, heavy deposit on walls | − | − |
| 0.02 polymer | 5 and 10 | Increasing emulsification, still heavy deposit of oil on walls | + | + |
| 0.05 polymer | 5 and 10 | Two emulsions were formed: top emulsion rich on oil phase with big droplets and bottom emulsion with very fine droplets of oil dispersed in water phase | 2-5 mm | 1.7 μ |

TABLE 10

| Emulsifier in water % (w/w) | "Bunker C" oil % (v/v) | Type of Emulsion | Droplet size (diameter) | |
|---|---|---|---|---|
| | | | top * | bottom ** |
| 0.05 and 0.1 ferm.broth | 5 and 10 | No emulsification, "Bunker C" oil deposited on walls | − | − |
| 1.0 ferm.broth | 5 and 10 | Good emulsification, top layer of emulsion contained big droplets of oil. | + | 2.1 μ |
| 2.0 ferm.broth | 5 and 10 | Very good emulsification, only thin layer emulsion with big droplets of oil | + | 1.69 μ |
| 3.0 ferm.broth | 5 and 10 | Still good emulsification but worse than with 1 and 2% - probably overdosage | + | + |

A similar set of experiments were conducted in an artificial sea water medium and the results are shown in Table 11. Emulsification was tested at two different temperatures: 7° C and 25° C. The concentrations of polymer were 0.05 and 0.1% (w/w), the concentrations of fermentation broth were 0.5, 1.0 and 2.0% (w/w) and the concentration of cells+ polymer precipitated from fermentation broth were 0.5, 1.0 and 2.0% (w/w). The test systems contained 90 ml of aqueous polymer product and 10 ml of Bunker C oil.

TABLE 11

| Emulsifier in sea water % (w/w) | Temp. °C | Type of emulsion | Droplet size (diameter) top * | bottom ** |
|---|---|---|---|---|
| 0.05 polymer | 7 | Emulsification only on top into big droplets | 5 mm | — |
|  | 25 | Two types of emulsion | 3–5 mm | 1.77 μ |
| 0.1 polymer | 7 | Two types of emulsion | 1–3 mm | 1.55 μ |
|  | 25 | Two types of emulsion | 1–3 mm | 1.68 μ |
| 0.5 ferm.broth | 25 | Two types of emulsion | 2–3 mm | 1.9 μ |
| 1.0 ferm.broth | 25 | Emulsification only on top | 5 mm | — |
| 2.0 ferm.broth | 7 | Two types of emulsion | 1–3 mm | 1.7 μ |
|  | 25 | Emulsification only on top | 5 mm | — |
| 0.5 polymer + cells | 7 | Homogeneous emulsions, only few big droplets of oil on top | + | 1.8 μ |
|  | 25 |  | + | 1.87 μ |
| 1.0 | 7 | At 7° C the emulsification was completed in 72 hrs, at 25° C in 24 hrs. | + | 1.66 μ |
|  | 25 |  | + | 2.16 μ |
| 2.0 | 7 |  | + | 1.56 μ |
|  | 25 |  | + | 1.5 μ |

In general, emulsification in sea water was not quite as good as was observed in fresh water. However, the test results are favourable. A concentration of 0.1% pure polymer gave 1–3 mm diameter droplets in the top layer and 1.55–1.68 μ droplet in the bottom layer. The degree of emulsification of Bunker C oil with fermentation broth gave droplets in the top phase of 1–5 mm and droplets in the bottom phase varying from 0–1.9 μ. Although the 2.0% fermentation broth contains > 0.05% polymer, the emulsification was not as good. Interferences can be attributed to salts in the broth, cells and other organic intermediates present. Crude polymer and cells precipitated from broth gave excellent emulsification at both 7° and 25° C.

In all instances agitation and mixing became more important as the temperature is lowered.

Although the use of these agents has only been evaluated and described in connection with specific hydrocarbon materials it will be understood by those skilled in the art that they are usable also with other materials commonly requiring emulsification such as steroids, oils and fats, specifically corn oil, soya bean oil, beef, lard, etc. They may also be used in association with other materials in applications for example such as the removal of oily stains from clothing and other fabrics.

TAXONOMY OF THE CULTURE

The culture is a Gram-positive bacterium which shows snapping division and becomes coccoid forming cystites after 48 hrs. It fits well in the family of Corynebacteriaceae and since it does not utilize cellulose, it cannot be placed in the genus Cellulomonas. It differs from the genus desciption of Corynebacterium by being strongly urease positive, catalase positive, and gelatinase negative. It is similar to Corynebacterium hydrocarboclastus (Iizuka and Komogata, 1964) in that growth is observed on glucose, lactose, xylose, as well as in other major characteristics described. Urease activity has not been reported for this microbe. This culture is also similar to Arthrobacter luteus as described by Kaneko et al. (1969). It differs by showing negative gelatin liquefaction, alkaline reaction in milk, no production of nitrite from nitrate, and no acid production from carbohydrates. Because it fits best into the genus description of Corynebacterium and differs from Arthrobacter by being urease positive and always Gram positive, it has been placed in the genus Corynebacterium. Except for urease production, which has not been reported, the culture possesses all the characteristics of Corynebacterium hydrocarboclastus.

The following Table 12 summarizes various tests that were carried out in the establishment of the taxonomy of the culture.

Viable samples of the culture have been deposited in fulfillment of the requirements of 35 U.S.C. 112 in August, 1972 in the culture collection of the University of Western Ontario, London, Ontario, Canada and have been given the reference number 409. Another deposit has been made with the Northern Utilization Research and Development Division of the Agricultural Research Service of the United States Department of Agriculture, Peoria, Illinois, and has been assigned designation NRRL-B-5631. A further deposit has been made with U.S. Army Natick Laboratories, Natick, Mass.

TABLE 12

| TESTS | CORYNEBACTERIUM HYDROCARBOCLASTUS |
|---|---|
| appearance | gram positive bacillus - 24 hrs |
|  | gram positive breeded bacillus - 70 hrs |
|  | gram positive cocci - 96 hrs |
|  | (on yeast glucose at 25° C) |
| arabinase | growth but fermentation negative |
| dulcitol | growth but fermentation negative |
| glucose | growth but fermentation negative |
| glycerol | growth but fermentation negative |
| lactose | growth but fermentation negative |
| maltose | growth but fermentation negative |
| mannitol | growth but fermentation negative |
| salicin | growth but fermentation negative |
| sucrose | growth but fermentation negative |
| xylose | growth but fermentation negative |
| gelatin | growth - not liquified |
| milk | alkaline - no pept., no coagulation |
| nitrate-nitrite | growth - negative reaction |
| indole | growth - negative reaction |
| urea | strong reaction - 24 hrs |
| oxidation - fermentation reaction (D-F) | growth - no reaction |
| motility | negative |
| oxidase | negative |
| catalase | positive |
| odor | urea medium - ammonium |
|  | yeast glucose - sweet |
|  | gelatin -putrid |
| $H_2S$ | negative |
| growth on MacCankey medium | varied from no growth to slight growth |
| Pellicle | item pectile on all broths |
| acid fast stain | negative |

TABLE 12-continued

| TESTS | CORYNEBACTERIUM HYDROCARBOCLASTUS |
|---|---|
| starch utilization | negative - 48 hrs. Negative after five days incubation. |
| capsule | present |

The polymer fraction of the Corynebacterium hydrocarboclastus reaction product behaves as a typical polyelectrolyte and the viscosity of the polymer solution decreases sharply upon addition of salts, as is illustrated by the following table 13 showing the effect of adding two different salts, sodium and calcium chloride thereto.

TABLE 13

| NaCl [g/100 ml] | Viscosity [cp] of solution of 0.5% (w/w) polymer | CaCl$_2$ [g/100 ml] | Viscosity [cp] of solution of 0.5% (w/w) polymer |
|---|---|---|---|
| 0 | 110 | 0 | 110 |
| 1 | 12 | 1 | 13 |
| 5 | 9 | 5 | 10 |
| 10 | 9 | 10 | 11 |
| 15 | 8 | 15 | 11.5 |
| 20 | 8 | 20 | 12 |

The emulsification by the polymer fraction of Corynebacterium hydrocarboclastus is effected by the pH of the solution and an acidic pH enhances the emulsification. For example kerosene was emulsified after ½ hour of agitation into a homogeneous emulsion at pH 3, into nonhomogeneous emulsions at pH 5, 7 and 9 and into an unstable emulsion at pH 11 at the concentration of 0.05% polymer (w/w). A mixture of "kerosene: Bunker C fuel oil" (1:9) was emulsified into homogeneous emulsions at pH 3, 5, 7, into a nonhomogeneous emulsion at pH and no emulsion was formed at pH 11, also at the concentration 0.05% polymer (w/w).

The interfacial tension between polymer solution and oil was effected in a similar manner in comparison with a control (water and oil). The results are summarized in Table 14 below.

TABLE 14

| | | interfacial tensions | | |
|---|---|---|---|---|
| pH | oil or mixture of oils | water/oil $\gamma_{w/o}$[dyn/cm] | 0.05% pol.sol/oil $\gamma_{p.s./o}$[dyn/cm] | $\gamma_{w/o}-\gamma_{p.s/o}$ |
| pH 3 | kerosene | 35.6 | 28.8 | 6.8 |
| | kerosene: bunker C oil (9:1) | 22.8 | 14.65 | 8.15 |
| | kerosene: bunker C oil (1:1) | 24.8 | 14.65 | 9.6 |
| | kerosene: bunker C oil (1:1) | — | 14.5 (NaCl sol.) | — |
| pH 7 | kerosene | 39.9 | 38.1 | 1.8 |
| | kerosene: bunker C oil (9:1) | 22.8 | 20.3 | 2.5 |
| | kerosene: bunker C oil (1:1) | 24.8 | 22.8 | 2.0 |
| | kerosene: bunker C oil (1:1) | — | 22.7 (NaCl sol.) | — |
| pH 10 | kerosene | 38.2 | 38.8 | 0.6 |
| | kerosene: bunker C oil (9:1) | 20.3 | 19.85 | 0.45 |
| | kerosene: bunker C oil (1:1) | 22.8 | 22.1 | 0.7 |
| | kerosene: bunker C oil (1:1) | — | 22.1 (NaCl sol.) | — |

We claim:

1. A process for the production of an emulsifying agent of microbiological origin which will effect emulsification of hydrocarbon fuels in water, comprising the step of cultivating by an aerobic fermentation in aqueous nutrient solution and with paraffinic hydrocarbon substrate as principal source of assimilable carbon a micro-organism having all the characteristics of Corynebacterium hydrocarboclastus UWO409 or NRRL-B-5631 until the fermentation medium contains at least 0.1% by weight of an active emulsification agent consisting of an extra-cellular polymer comprising a polysaccharide and a bound protein component, formed as a result of the fermentation.

2. A process as claimed in claim 1, wherein the fermentation is continued until the fermentation medium contains up to about 2% of the said extra-cellular polymer.

3. A process as claimed in claim 2, wherein the polysaccharide component of said extra-cellular polymer includes galactose, glucose and mannose units.

4. A process as claimed in claim 3, wherein the said polysaccharide component includes galactose, glucose and mannose in the ratio 1:2.65:1.96.

5. A process as claimed in claim 1, and including the step of removing from the fermentation medium the unused hydrocarbon substrate and the insoluble cellular material.

6. A process as claimed in claim 3, and including the step of separating the extra-cellular polymer from the fermentation medium.

7. A process as claimed in claim 6, and including the step of separating from the extra-cellular polymer components thereof of molecular weight less than 20,000.

8. A process as claimed in claim 1, wherein the fermentation medium contains from about 1 to 2% by volume of paraffinic hydrocarbon.

9. A process as claimed in claim 2, wherein the principal source of nitrogen in the aqueous solution is sodium nitrate.

10. An emulsifying agent of microbiological origin consisting essentially of the extra-cellular polymer product of an aqueous aerobic fermentation employing a micro-organism having all the characteristics of Corynebacterium hydrocarboclastus UWO409 or NRRL-B-5631 with paraffinic hydrocarbon substrate, the said polymer comprising a polysaccharide component including primarily galactose, glucose and mannose in the ratio about 1:2.65:1.96 and a bound protein component the polymer containing about 1 to 4.2% by weight organic nitrogen and about 30 to 35% by weight carbohydrate.

11. The invention as claimed in claim 10, in solution in an aqueous medium in amounts up to about 2% by weight of the aqueous medium.

12. The invention as claimed in claim 10, wherein the bound protein component has glycine, alanine and aspartic acid as its principal amino acids.

13. The invention as claimed in claim 10, wherein the polysaccharide component contains 17.8% galactose, 74.2% glucose and 35% mannose, and the protein component contains about 14% glycine, about 13% alanine and about 12% aspartic acid.

14. The invention as claimed in claim 10, wherein the molecular weight of the said polymer product is greater than 20,000.

15. The invention as claimed in claim 10, wherein the microorganism is UWO409 or NRRL-B-5631.

* * * * *